(12) United States Patent
Heeren

(10) Patent No.: US 10,039,669 B2
(45) Date of Patent: Aug. 7, 2018

(54) INTERNALLY ILLUMINATED SURGICAL PROBE

(71) Applicant: Novartis AG, Basel (CH)

(72) Inventor: Tammo Heeren, Aliso Viejo, CA (US)

(73) Assignee: Novartis AG, Basel (CH)

( * ) Notice: Subject to any disclaimer, the term of this patent is extended or adjusted under 35 U.S.C. 154(b) by 469 days.

(21) Appl. No.: 14/522,684

(22) Filed: Oct. 24, 2014

(65) Prior Publication Data

US 2016/0113722 A1    Apr. 28, 2016

(51) Int. Cl.
| A61B 1/06 | (2006.01) |
| A61F 9/007 | (2006.01) |
| A61B 3/00 | (2006.01) |
| A61B 90/30 | (2016.01) |

(52) U.S. Cl.
CPC ........ *A61F 9/00763* (2013.01); *A61B 3/0008* (2013.01); *A61B 90/30* (2016.02); *A61B 2090/306* (2016.02); *A61B 2217/005* (2013.01)

(58) Field of Classification Search
CPC .. A61B 1/06; A61B 1/07; A61B 10/02; A61B 10/04; A61B 3/0008; A61F 9/00763; A61M 2205/587; A61M 2025/0175; A61M 2025/0004; A61M 2005/3201
USPC .................................. 600/248, 249
See application file for complete search history.

(56) References Cited

U.S. PATENT DOCUMENTS

| 3,990,453 | A | 11/1976 | Douvas et al. |
| 4,168,707 | A | 9/1979 | Douvas et al. |
| 4,200,106 | A | 4/1980 | Douvas et al. |
| 5,281,214 | A | 1/1994 | Wilkins et al. |
| 5,425,730 | A | 6/1995 | Luloh |
| 5,651,783 | A | 7/1997 | Reynard |
| 5,667,472 | A | 9/1997 | Finn et al. |
| 5,733,297 | A * | 3/1998 | Wang ................... A61F 9/00763 606/167 |
| 6,939,341 | B2 | 9/2005 | Vijfvinkel |
| 7,972,326 | B2 | 7/2011 | Scheller |
| 8,075,553 | B2 | 12/2011 | Scheller et al. |
| 8,968,347 | B2 | 3/2015 | McCollam |
| 8,979,867 | B2 | 3/2015 | Peyman |
| 2009/0163897 | A1 | 6/2009 | Skinner |
| 2009/0182313 | A1* | 7/2009 | Auld ....................... A61B 17/28 606/15 |

(Continued)

FOREIGN PATENT DOCUMENTS

| GB | 1349881 A | 4/1974 |
| WO | 2004/002337 A1 | 1/2004 |
| WO | 2016/064580 A1 | 4/2016 |

OTHER PUBLICATIONS

Calhoun, et al., The Roto-Extractor in Pediatric Op;hthalmology, Tr. Am. Ophth. Soc., vol. LXXIII, 1975, (14 pages).

(Continued)

*Primary Examiner* — Si Ming Ku

(57) ABSTRACT

A surgical probe (e.g., for treating an eye of a patient) includes a body, a cutting element extending distally from the body including a sleeve member comprising a port at an end, and an inner member disposed within the sleeve member, the inner member being movable (e.g., axially) with respect to the sleeve member to open and close the port. The probe further includes an illumination element disposed within the sleeve member, the illumination element configured to project light out of the port.

13 Claims, 7 Drawing Sheets

(56) References Cited

U.S. PATENT DOCUMENTS

| | | |
|---|---|---|
| 2011/0282160 A1 | 11/2011 | Bhadri et al. |
| 2014/0121469 A1 | 5/2014 | Meckel et al. |
| 2014/0357957 A1 | 12/2014 | Bhadri et al. |

OTHER PUBLICATIONS

Douvas, Microsurgical Roto-Extractor Instrument for Vitrectomy, New Research on the Aetiology and Surgery of Retinal Detachment Mod. Probl. Ophthyal., vol. 15, pp. 253-260 (Karger, Basel 1975), Port Huron, Michigan, USA (8 pages).
DORC: Focus on New Instruments 2009/2010 catalog; Version 2009.1: Copyright 2009 D.O.R.C. International b.v. Dutch Ophthalmic USA Inc. (4 pages).
Museum of Vision: Collection Objects; The Foundation of the American Academy of Ophthalmology; http://www.museumofvision.org/collection/artifacts?accession=2004.004.00001; Technology dated 1970 (4 pages).
Alcon Vitreoretinol Product Catalog 2009, pp. 27-28 (2 pages).
Meadow, MD, FACS; Norman B.; Vitreous history in the making; Ophthalmology Times, Jul. 15, 2013 (3 pages).

* cited by examiner

INTERNALLY ILLUMINATED SURGICAL PROBE

FIELD OF THE INVENTION

The present disclosure relates to apparatuses and methods for ophthalmic medical procedures, and more particularly, to apparatuses and methods including vitreous fluid illumination.

BACKGROUND

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself Delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard vitrectomy probes typically include a hollow needle with a port on the end to pull in vitreous fibrils. An inner member, placed within the hollow needle, moves back and forth to open and close the port. This operates to cut any fibrils that enter the port while it is open.

Typically, the surgeon uses a separate fiber optic illuminator probe when performing a vitrectomy. The illuminator probe is used to provide oblique illumination of the vitreous for distinction from other fluids within the eye. Without such illumination, such other fluids may be indistinguishable from the vitreous fibrils. Manipulation of both the vitrectomy probe and the illuminator probe can be difficult. Additionally, use of the illuminator probe may require an additional incision in the patient's eye for insertion of the illuminator probe. There is a need for continued improvement in the use and operability of vitrectomy probes. The probes discussed herein are arranged to address one or more of the deficiencies in the prior art.

SUMMARY

This disclosure relates generally to, and encompasses, apparatuses and methods for removing fluid from the eye, and more specifically to ophthalmic surgical systems and methods of using the systems to remove fluid from the eye.

According to some embodiments, a surgical probe (e.g., an ophthalmic surgical probe for treating an eye of a patient) includes a body, a cutting element extending distally from the body including a sleeve member comprising a port at an end, and an inner member disposed within the sleeve member, the inner member being movable (e.g., axially) with respect to the sleeve member to open and close the port. The probe further includes an illumination element disposed within the sleeve member, the illumination element configured to project light out of the port.

According to some embodiments, a surgical system (e.g., an ophthalmic surgical system) includes a probe having a body and a cutting element extending distally from the body, the cutting element including a sleeve member comprising a port at an end, an inner member disposed within the sleeve member, and an actuating element configured to move the inner member (e.g., axially) with respect to the sleeve member to open and close the port. The probe further includes an illumination element disposed within the sleeve member, the illumination element configured to project light out of the port. The system further includes a console comprising a light source in optical communication with the illumination element of the probe.

According to some embodiments, a method for using a surgical probe (e.g., a vitrectomy probe) includes reciprocally actuating an inner member of a cutting element with respect to a sleeve member of the cutting element, the inner member being positioned within the sleeve member, the sleeve member extending distally from a body of a probe, the sleeve member comprising a port positioned such that actuating of the inner member opens and closes the port, and projecting light from an illumination element to a region outside the port, the illumination element being disposed within the sleeve member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
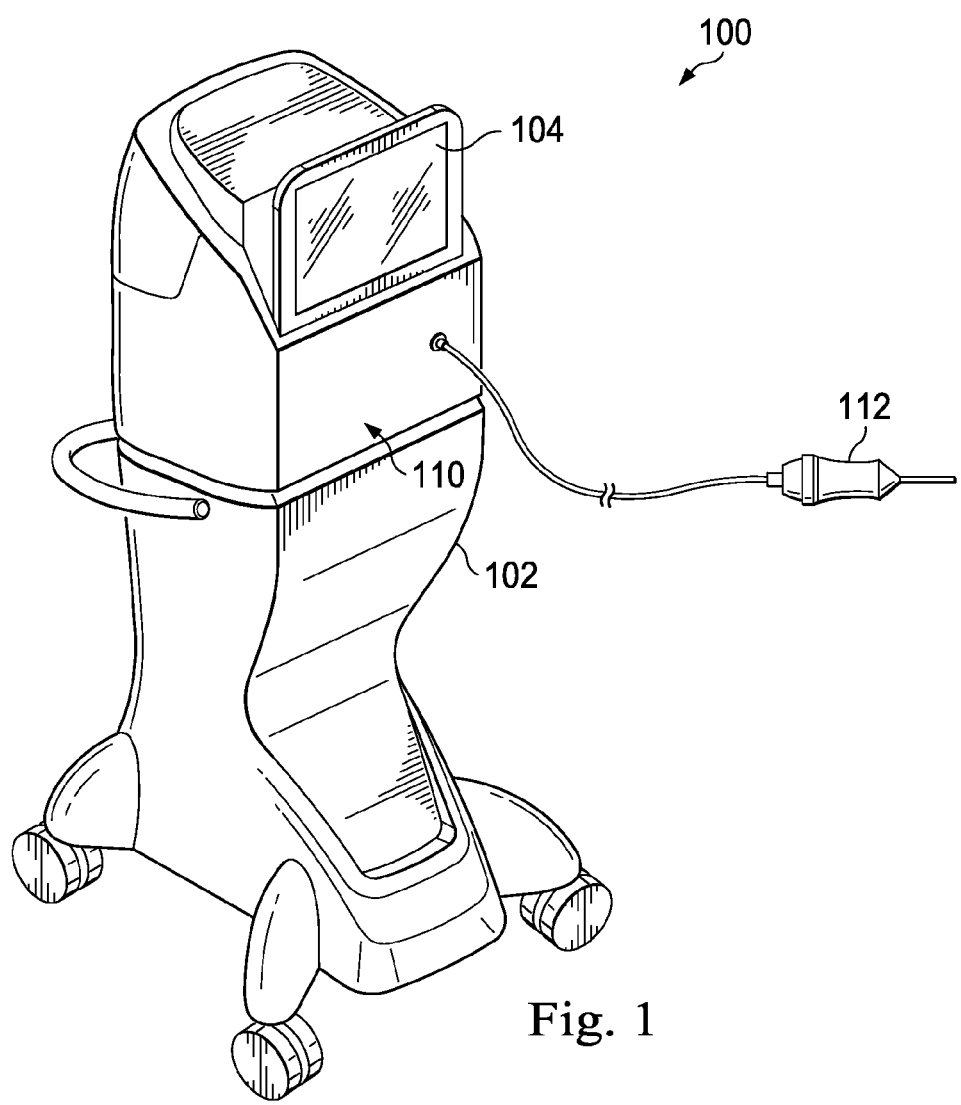
FIG. 1 is a diagram showing an illustrative surgical probe system according to one example incorporating the principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for removing tissue and/or fluid from a body (e.g., removing ocular tissue and/or fluid from the eye). The various figures show embodiments of exemplary surgical probes (e.g., ophthalmic surgical probes) and methods of using the devices to remove tissue and/or fluid from a patient. Embodiments described herein incorporate an illumination element that may operate to illuminate vitreous and provide visual enhancement to a surgeon performing a procedure. While several embodiments are presented herein for removing vitreous from a patient's eye, one of ordinary skill in the art, would understand that similar embodiments could be used to remove tissue and/or fluid from other locations in the body without departing from the general intent or teachings of the present disclosure.

FIG. 1 is a diagram showing an illustrative vitrectomy surgical system 100. According to the present example, the vitrectomy surgical system 100 includes a base housing 102 and an associated display screen 104 showing data relating to system operation and performance during a vitrectomy surgical procedure. In this exemplary embodiment, the vitrectomy surgical system 100 includes a mobile console that may be used by a health care provider to perform a vitrectomy surgical procedure. The vitrectomy surgical system 100 includes a vitrectomy probe 112 and is configured to be used during an ophthalmic surgical procedure, such as, for example, a vitrectomy surgical procedure. The base housing 102 may be configured to process, receive, and store data and provide signals to the vitrectomy probe and/or the display 104.

Figure 2:
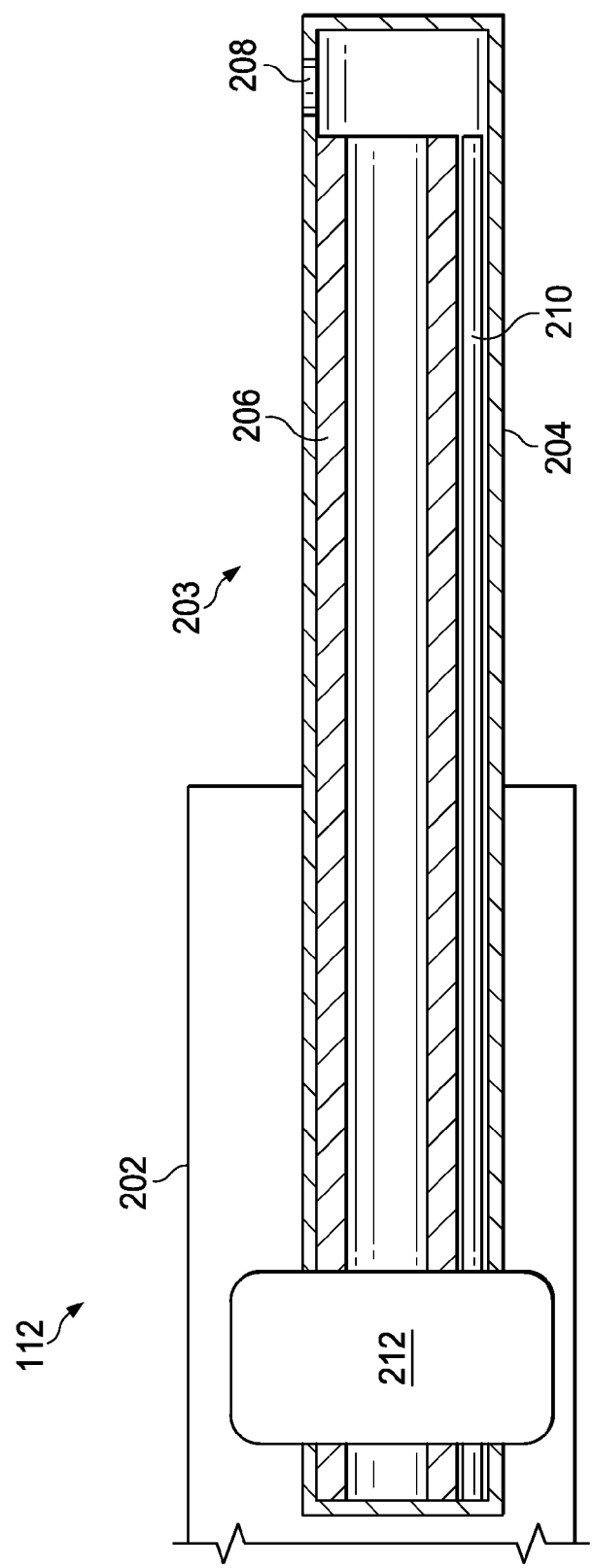
FIG. 2 is a diagram showing an illustrative longitudinal cross-sectional view of a portion of surgical probe with internal illumination according to one example incorporating the principles described herein.

FIG. 2 is a stylized diagram showing a portion of the illustrative vitrectomy probe 112 with internal illumination. FIG. 2 shows a longitudinal cross-sectional view of the vitrectomy probe 112. According to the present example, the vitrectomy probe 112 includes a body 202, which is shown in part. The body 202 supports a cutting element 203 that includes a sleeve member 204, an inner member 206, and an illumination element 210.

The body 202 may be made from a variety of materials commonly used to form such tools. For example, the body 202 may be made of, for example, a lightweight aluminum or plastic. The exterior portion of the body 202 may be ergonomically designed for comfortable grasping by a surgeon or operator of the vitrectomy probe 112. The inner portion of the body 202 is designed to support the cutting element 203 and other features that may be included with the probe 112.

The cutting element 203 includes the inner member 206 and the sleeve member 204. The sleeve member 204 is a hollow needle designed to enter a patient's eye. The sleeve member 204 includes a port 208 at the distal end. The port 208 is disposed along the side of the distal end as illustrated. The port 208 may be a square, rectangular, circular, elliptical, or other shaped opening. The opening is designed to allow vitreous fibrils from the patient's eye to enter. Movement (e.g., axial, rotational, etc.) of the inner member 206 within the sleeve member 204 operates to open and close the port 208, thereby cutting any vitreous fibrils that enter the port 208 while it is open.

The inner member 206 of the cutting element 203 is a hollow tube that operates as the cutter portion of the vitrectomy probe 112. Thus, the end of the inner member 206 is sufficiently sharp to cut vitreous fibrils. The inner member 206 may be made from a variety of materials, including for example, stainless steel and others. In some cases, the inner member 206 may include multiple members attached together. For example, the distal end of the inner member 206 may be a cutter member made of a different material than the proximal end. The proximal end of the inner member 206 may be connected to an actuating element 212 that moves the inner member 206 with respect to the sleeve member 204.

The illumination element 210 is arranged to provide oblique illumination of vitreous fibrils outside the cutting element 203 from within the cutting element 203. Thus, a vitrectomy procedure can be performed without the use of a separate illuminator probe. Alternatively, the internally illuminated probe may be used to supplement light from a separate illuminator probe. The illumination element 210 is arranged to project light from within the cutting element 203 through the port 208. Thus, the illumination element 210 can be positioned such that light is projected from the port 208 in an advantageous manner.

In some embodiments, the illumination element 210 is an optical fiber having an illuminating portion. The optical fiber may extend from a console, such as console 102, to the distal end of the probe 112. The optical fiber may be designed to propagate a sufficient amount of light so as to adequately illuminate the vitreous fibrils during a vitrectomy procedure. As will be described in further detail below, the illumination element 210 may be secured to either the inner member 206 or the sleeve member 204.

Figure 3A:
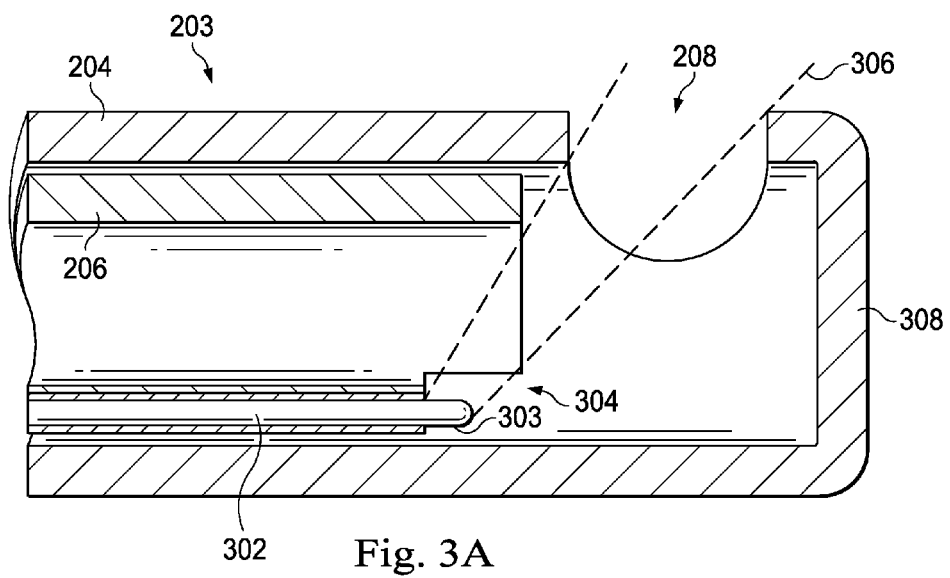
FIGS. 3A and 3B are diagrams showing illustrative longitudinal cross-sectional views of a surgical probe with an illumination element secured to an inner member according to one example incorporating the principles described herein.
Figure 3B:
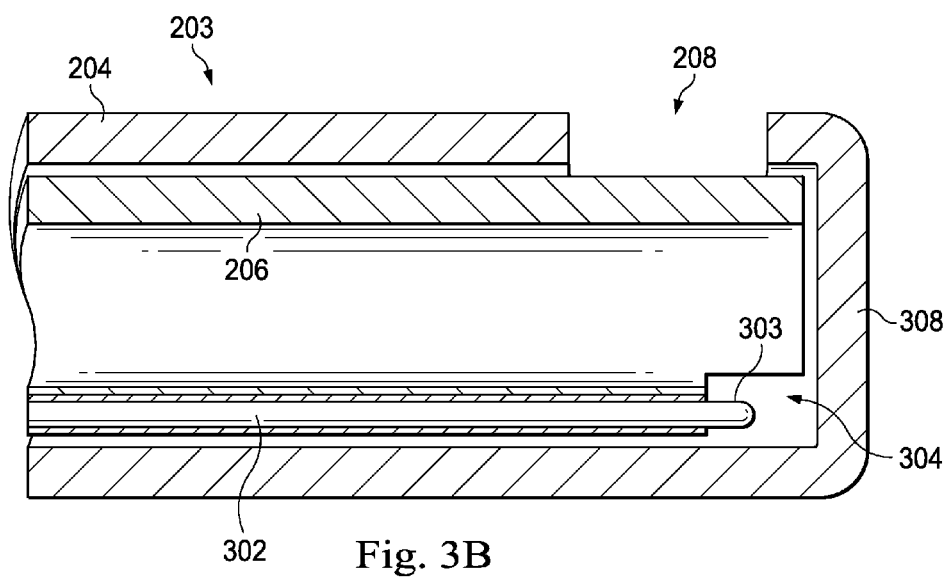

FIGS. 3A-3B are diagrams showing an illustrative longitudinal cross-sectional view of a vitrectomy probe 112 with an illumination element 302 secured to the inner member 206. Thus, the illumination element 302 moves with the inner member 206. According to the present example, the illumination element 302 includes an illuminating portion 303 and is secured to the inner member 206 on a side that is opposite of the port 208. The illuminating portion 303 is therefore arranged to direct light across the open end of the inner member 206 towards the port 208. Thus, light 306 from the illuminating portion 303 of the illumination element 302 can be more efficiently projected out of the port 208. FIG. 3A illustrates the inner member 206 in a position that is proximal of the port 208. FIG. 3B illustrates the inner member 206 in a position that is distal of the port 208.

The illumination element 302 may be secured to the inner member 206 in a variety of ways. For example, the inner member 206 may include a channel (not shown) in which the illumination element 302 is placed. Particularly, in the example where the illumination element 302 is a fiber optic cable, the fiber optic cable may run through the channel of the inner member 206 until it terminates at the distal end of the inner member 206. The illumination element 302 may also be bonded to the surface of the inner member 206. A surface of the illumination element 302 may include a material that is selected to have less friction with the inner surface of the sleeve member 204. Thus, as the inner member 206 moves with respect to the sleeve member, the illumination element 302 is less prone to damage.

In one example, a notch 304 is formed within the inner member 206 at the distal end of the inner member 206. The notch 304 is positioned between the illumination element 304 and the port 208. The notch 304 may be designed to expose the illuminating portion 303 which is shown as a side of an optical fiber of the illumination element 302. Thus, light 306 may be emitted in the direction of and projected out of the port 208.

The illumination element 302 may be designed to project light in a manner that is convenient for an operator of the probe 112. For example, during a vitrectomy procedure, it is preferable to have light projected in an oblique manner with respect to the position of the operator. If light is projected back towards the operator, it can cause a glare that makes it difficult for the operator to view the illuminated vitreous fibrils. Moreover, during the vitrectomy procedure, the operator of the probe 112 may rotate the cutting element 203 in various positions to effectively remove all the vitreous fibrils. Thus, the illumination element 302 can be designed to project light 306 out of the port 208 and angled towards the distal end 308 of the cutting element 203. Here, the light projected out of the port is angled obliquely and in a distal direction. The side of the inner member 206 may prevent light from being emitted in a direction directly transverse to the axial direction. This allows the operator to use the probe 112 at a variety of angular positions without having light projected back at the operator.

When the distal end of the inner member 206 is positioned proximal of the port 208, as illustrated in FIG. 3A, vitreous fibrils are able to enter the port 208. Additionally, the light 306 from the illumination element 302 exits the port 208 to provide oblique illumination of vitreous fibrils outside of the port 208. As described above, the inner member 206 reciprocally actuates axially with respect to the sleeve member 204 to open and close the port 208. As the port 208 is closing, any vitreous fibers within the port are severed. The severed fibrils can then be aspirated through the hollow inner member 206.

When the distal end of the inner member 206 is positioned distal of the port 208, as illustrated in FIG. 3B, the illumination element 302 no longer projects light 306 out of the port 208. While the light source may be maintained, and the light still be projected out of the illumination element, the inner member 206 is positioned such that the light is not directed out of the port 208. The inner member 206 may move with respect to the sleeve member 204 at a rate within the range of 5,000 to 10,000 cycles per minute, for example. Because the inner member 206 moves at such a rate, the light 306 is interrupted at a frequency that is too high to be detected by the human eye. Thus, the operator of the probe is provided with a seemingly steady light source with which to view the vitreous fibrils.

Figure 4A:
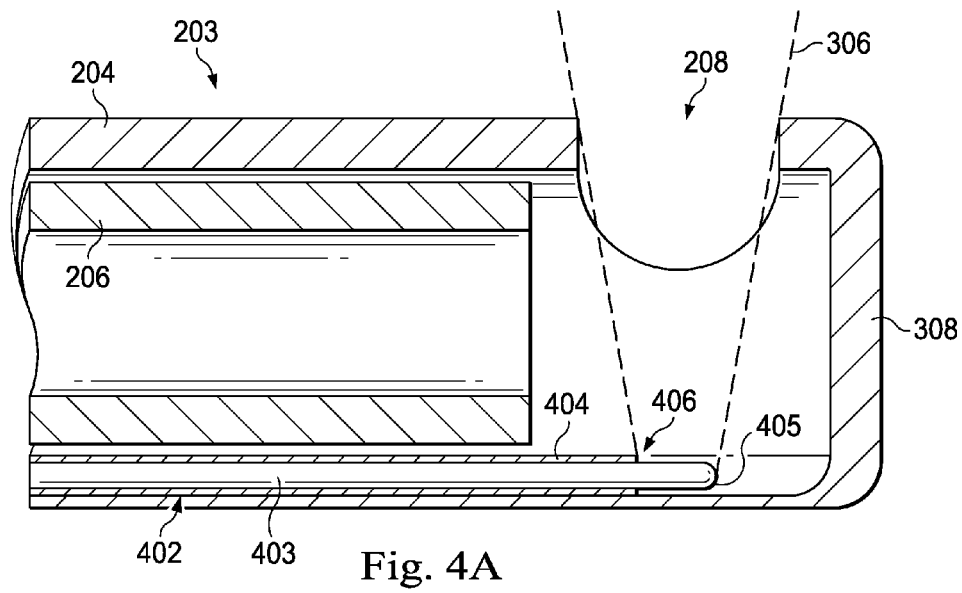
FIGS. 4A and 4B are diagrams showing illustrative longitudinal cross-sectional views of a surgical probe with an illumination element secured to a sleeve member according to one example incorporating the principles described herein.
Figure 4B:
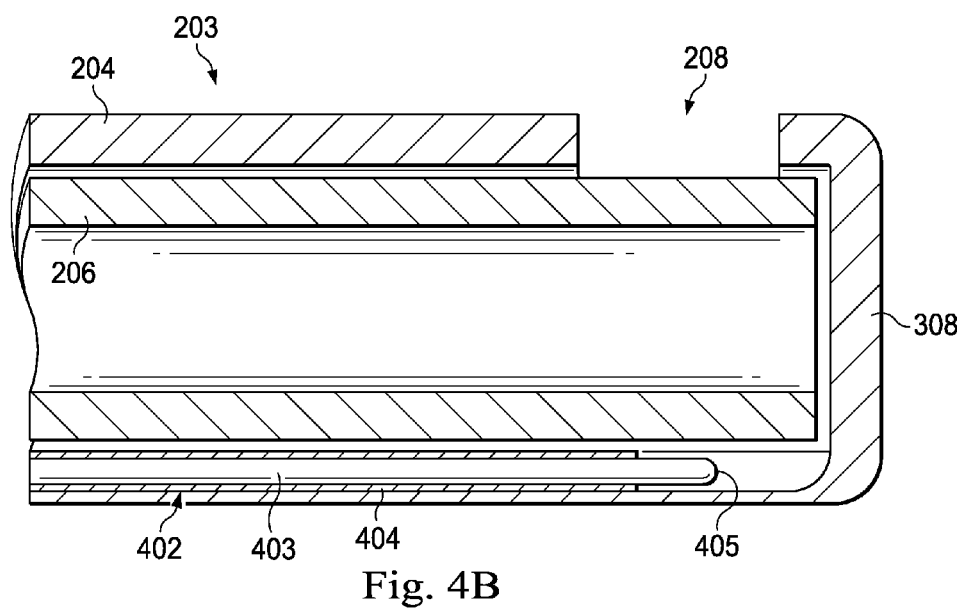

FIGS. 4A-4B are diagrams showing an illustrative longitudinal cross-sectional view of a vitrectomy probe with an illumination element 402 secured to the sleeve member 204. Thus, movement of the inner member 206 does not cause movement of the illumination element 402. According to the present example, the illumination element 402 is secured to the sleeve member 204 on a side that is opposite of the port 208. Thus, light 306 from the illumination element 302 can more efficiently be projected out of the port 208. FIG. 4A illustrates the inner member 206 in a position that is proximal of the port 208. FIG. 4B illustrates the inner member 206 in a position that is distal of the port 208.

The illumination element 402 may be secured to the sleeve member 204 in a variety of ways. For example, the sleeve member 204 may include a channel (not shown) in which the illumination element 402 is placed. Particularly, in the example where the illumination element 402 is a fiber optic cable, the fiber optic cable may run through the channel of the sleeve member 204 until it terminates near the port 208. The illumination element 402 may also be bonded to the surface of the sleeve member 204.

In one example, the illumination element 402 may be a fiber optic cable with a core 403 and a cladding 404. The cladding 404 has a lower refractive index than the core 404, thus allowing the fiber optic cable to act as an optical waveguide. The cladding may have a removed portion 406 on a side of the cable near the distal end forming an illuminating portion 405. Thus, light 306 is projected from the illuminating portion 405 substantially perpendicular to the axis of the cable, allowing it to be projected out of the port 208.

Like illumination element 302, illumination element 402 may be designed to project light in a manner that is convenient for an operator of the probe 112. Specifically, the illumination element 402 can be designed to project light out of the port 208 and angled towards the distal end 308 of the cutting element 203. In FIG. 4, it accomplishes this by arranging the illumination portion 405 at a location proximal of the port 208. Thus, the operator is able to use the probe 112 at a variety of angular positions without having light projected back at the operator.

When the distal end of the inner member 206 is positioned proximal of the port 208, as illustrated in FIG. 4A, the light 306 from the illumination element 402 exits the port 208 to provide oblique illumination of vitreous fibrils outside of the port 208. As described above, the inner member 206 reciprocally actuates axially with respect to the sleeve member 204 to open and close the port 208. As the port 208 is closing, any vitreous fibers within the port are severed. The severed fibrils can then be aspirated through the hollow inner member 206.

When the distal end of the inner member 206 is positioned distal of the port 208, as illustrated in FIG. 4B, the illumination element 402 is blocked by the inner member 206 and no longer projects light 306 out of the port 208. But, as described above, the inner member 206 may move with respect to the sleeve member 204 at a rate within the range of 5,000 to 10,000 cycles per minute, for example. Because the inner member 206 moves at such a rate, the light 306 is interrupted at a frequency that is too high to be detected by the human eye. Thus, the operator of the probe is provided with a seemingly steady light source with which to view the vitreous fibrils.

Figure 5A:
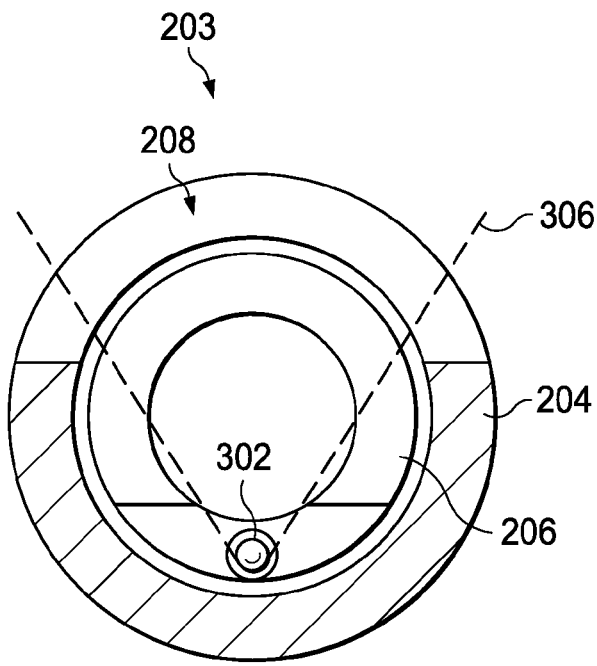
FIGS. 5A and 5B are diagrams showing axial cross-sectional views of exemplary surgical probes with one or more illumination elements secured to the inner member according to examples incorporating the principles described herein.
Figure 5B:
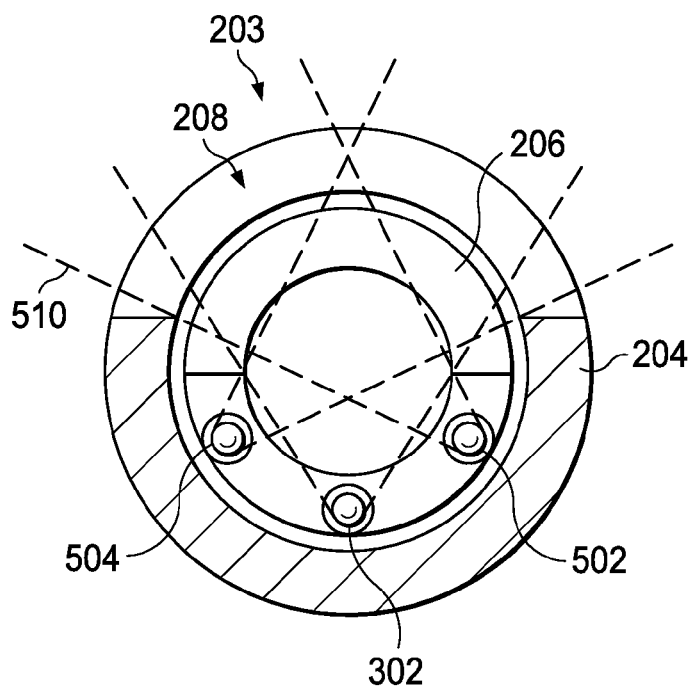

FIGS. 5A-5B are diagrams showing axial cross-sectional views of vitrectomy probes with one or more illumination elements secured to the inner member 206. FIG. 5A illustrates an axial cross-sectional view of a vitrectomy probe with a single illumination element 302 secured to the inner member 206 and placed at an opposite side from the port 208. This may be the same probe shown in FIGS. 3A and 3B. Thus, the light 306 can be efficiently projected out of the port 208. It is contemplated that the single illumination element 302 can be placed at other locations along the circumference of the inner member 206 such that light can be directed out of the port 208.

FIG. 5B illustrates an axial cross-sectional view of a vitrectomy probe with multiple illumination elements 302, 502, 504 secured to the inner member 206. Use of multiple illumination elements positioned around the circumference of the inner member 206 may result in a wider illumination profile 510. In some embodiments, even more illumination elements may be included. Each of the illumination elements 302, 502, 504 may be secured to the inner member 206 in a manner as described above in the text accompanying FIGS. 3A-3B. Additionally, the inner member 206 may include a notch (e.g., 304, FIGS. 3A-3B) for each of the illumination elements 302, 502, 504 that allows light from the respective illumination element to be directed out of the port 208.

Figure 6A:
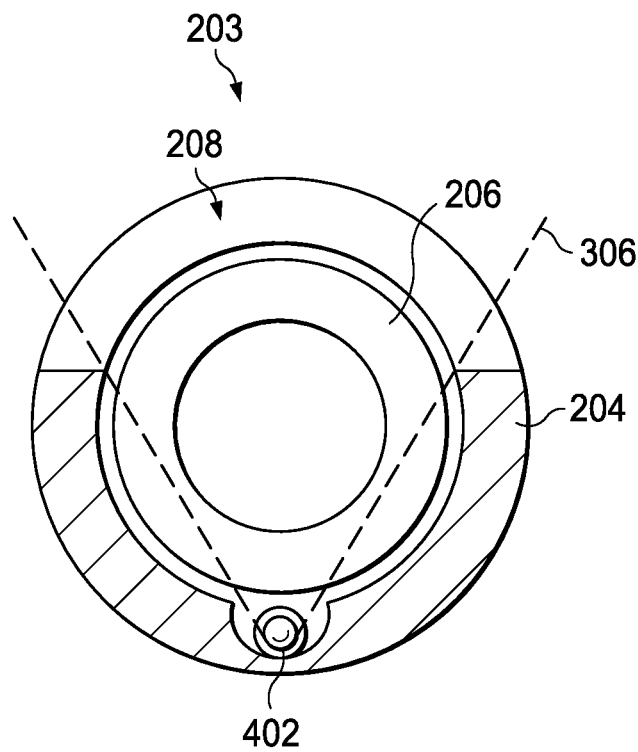
FIGS. 6A and 6B are diagrams showing axial cross-sectional views of exemplary surgical probes with one or more illumination elements secured to the sleeve member according to examples incorporating the principles described herein.
Figure 6B:
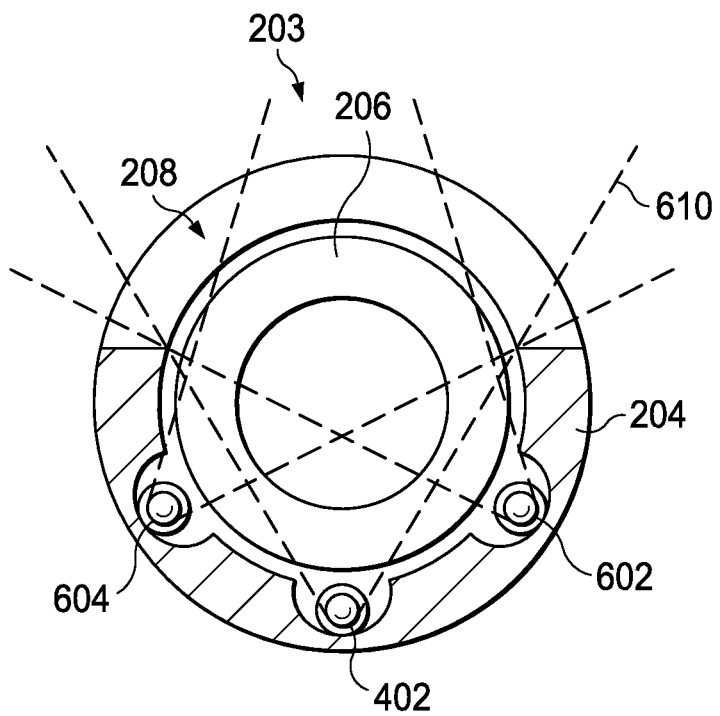

FIGS. 6A-6B are diagrams showing axial cross-sectional views of vitrectomy probes with one or more illumination elements secured to the sleeve member 204. FIG. 6A illustrates an axial cross-sectional view of a vitrectomy probe with a single illumination element 402 secured to the sleeve member 204 and placed at a side that is opposite from the port 208. Thus, the light 306 can be efficiently projected out of the port 208. This probe may be the same probe shown in FIGS. 4A and 4B. It is contemplated that the single illumination element 402 can be placed at other locations along the circumference of the sleeve member 204.

FIG. 6B illustrates an axial cross-sectional view of a vitrectomy probe with multiple illumination elements 402, 602, 604 secured to the sleeve member 204. Use of multiple illumination elements positioned around the circumference of the sleeve member 204 may result in a wider illumination profile 610. In some embodiments, even more illumination elements may be included. Each of the illumination elements 402, 602, 604 may be secured to the sleeve member 204 in a manner as described above in the text accompanying FIGS. 4A-4B. Additionally, each of the illumination elements 402, 602, 604 may have a corresponding portion of the cladding removed (e.g., 406, FIGS. 4A-4B) so that light from the respective illumination elements is appropriately directed out of the port 208.

Figure 7:
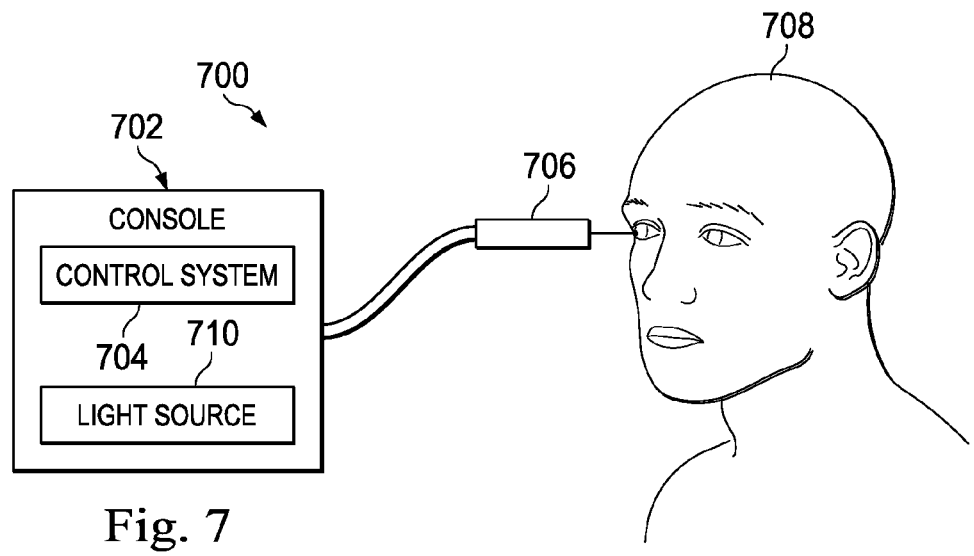
FIG. 7 is a diagram showing a surgical system with an internally illuminated surgical probe performing a surgical procedure on a patient according to one example incorporating the principles described herein.

FIG. 7 is a diagram showing an ophthalmic surgical system with an internally illuminated vitrectomy probe. According to the present example, the system 700 includes a console 702 and a hand piece 706. The console 702 includes a control system 704 and a light source 710. The hand piece 706 may be the same probe 112 discussed above, or may be another probe used by an operator or surgeon to treat a condition of the eye. In this example, the distal portion is inserted into the eye of a patient 708.

The console 702 includes all the necessary components to drive and work with the hand piece 706. Additional components and features of the console would be apparent to one of ordinary skill in the art. The control system 704 within the console 702 provides the desired signals to the hand piece 706 to cause the inner member to move with respect to the sleeve member and cut vitreous fibrils.

The light source 710 may provide light with sufficient luminosity so that when projected out of the illumination element of the hand piece 706, vitreous fibrils are sufficiently visible to the operator of the hand piece 706. The light may also have a selected color temperature so as to best illuminate the vitreous fibrils.

Figure 8:
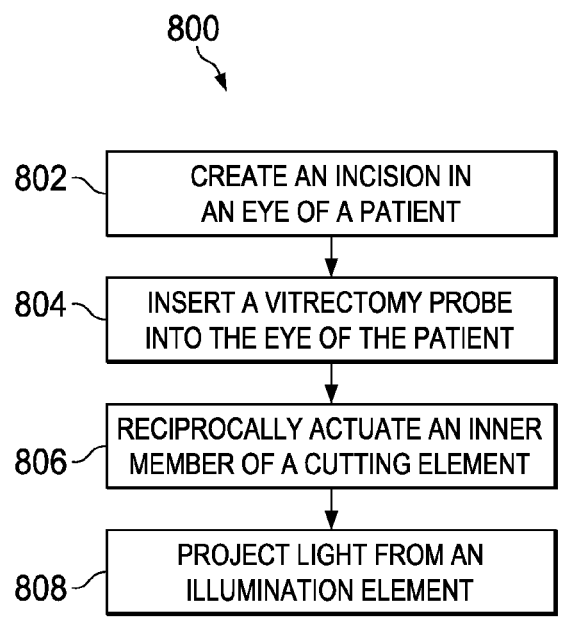
FIG. 8 is a flowchart showing an illustrative method for treating a patient with an internally illuminated surgical probe according to one example incorporating the principles described herein.

FIG. 8 is a flowchart showing an illustrative method 800 for treating a patient with an internally illuminated vitrectomy probe. According to the present example, the method 800 includes creating an incision in an eye of a patient at 802. At 804, the method 800 includes inserting a vitrectomy probe into the eye of the patient.

According to some examples, the probe includes an internal illumination element as described above. The probe also includes a cutting element having a hollow sleeve member extending distally from the body and an inner member within the hollow sleeve member.

At 806, the method 800 includes reciprocally actuating the inner member of the cutting element. For example, an actuating element secured to the inner member may move the inner member in the distal or proximal direction within the sleeve member. The movement opens or closes the port formed in the distal portion of the hollow sleeve member.

At 808, the method 800 includes projecting light from an illumination element. Element 808 may be performed simultaneously with 806. Specifically, light may be projected form the illumination element while the inner member moves axially with respect to the sleeve member. The light may be projected out of the port and angled to the distal end of the cutting element so as to provide oblique illumination of vitreous fibrils.

Other embodiments of the surgical systems having illuminated probes include illumination elements disposed along the inner member or the sleeve member on the same side as the port, and may be arranged with an illuminating portion that emits light in an oblique distal direction. Some of these embodiments emit light in a beam that includes light emission at a right angle relative to the axial direction. Other embodiments are also contemplated.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A surgical probe, the probe comprising:
   a body;
   a cutting element extending distally from the body including:
      a sleeve member comprising a port at an end, wherein the port is configured to receive tissue;
      an inner member disposed within the sleeve member, the inner member being movable across the port of the sleeve member, wherein the inner member is configured to cut the received tissue as the inner member moves across the port from a retracted position to a distal position inside the sleeve member; and
      an illumination element, disposed within the sleeve member, attached to the inner member such that the illumination element moves with the inner member inside the sleeve member, wherein the illumination element is configured to project light out of the port when the inner member is in the retracted position and wherein, when the inner member is in the distal position, the inner member inhibits light from the illumination element from projecting out of the port; wherein a distal end of an upper wall of the inner member, adjacent the port, extends past a distal end of a lower wall of the inner member, opposite the port, that is attached to the illumination element, wherein a distal end of the illumination element extends past the distal end of the lower wall of the inner member.

2. The surgical probe of claim 1, wherein the inner member comprises a notch on the distal end of the lower wall, the notch being positioned between an illuminating portion of the illumination element and the inner member and arranged so that light from the illuminating portion is directed towards the port.

3. The surgical probe of claim 1, wherein the illumination element is positioned on a side of the inner member that is opposite from the port.

4. The surgical probe of claim 1, wherein an illumination profile from the illumination element is directed out of the port and towards a distal end of the cutting element.

5. The surgical probe of claim 1, wherein the illumination element comprises a fiber optic cable.

6. The surgical probe of claim 5, wherein a light source for the illumination element is on a console connected to the body.

7. The surgical probe of claim 1, wherein the inner member is hollow and configured to aspirate vitreous fibrils from an eye of a patient.

8. The surgical probe of claim 1, wherein the illumination element is parallel to the inner member at the distal end of the inner member.

9. A surgical system comprising:
a probe comprising:
a body;
a cutting element extending distally from the body including:
a sleeve member comprising a port at an end, wherein the port is configured to receive tissue;
an inner member disposed within the sleeve member;
an actuating element configured to move the inner member across the port of the sleeve member, wherein the inner member is configured to cut the received tissue as the inner member moves across the port from a retracted position to a distal position inside the sleeve member; and
an illumination element, disposed within the sleeve member, attached to the inner member such that the illumination element moves with the inner member inside the sleeve member, wherein the illumination element is configured to project light out of the port when the inner member is in the retracted position and wherein, when the inner member is in the distal position, the inner member inhibits light from the illumination element from projecting out of the port, wherein a distal end of an upper wall of the inner member, adjacent the port, extends past a distal end of a lower wall of the inner member, opposite the port, that is attached to the illumination element, wherein a distal end of the illumination element extends past the distal end of the lower wall of the inner member; and
a console comprising a light source in optical communication with the illumination element of the probe.

10. The surgical system of claim 9, wherein the inner member comprises a notch on the distal end of the lower wall, the notch being positioned between an illuminating portion of the illumination element and the inner member and arranged so that light from the illuminating portion is directed towards the port.

11. The surgical system of claim 9, wherein the illumination element is positioned so as to direct light out of the port.

12. The surgical system of claim 9, wherein the console comprises a control system to cause the probe to:
actuate the inner member with respect to the sleeve member; and
project light from the illumination element during actuation.

13. The surgical system of claim 9, wherein the illumination element is configured to create an oblique illumination profile with respect to a longitudinal axis of the probe.

* * * * *